United States Patent
Liao et al.

(10) Patent No.: US 11,579,109 B1
(45) Date of Patent: Feb. 14, 2023

(54) METHOD OF CALCULATING DIELECTRIC CONSTANT AND DIELECTRIC LOSS OF POLYMER MATERIAL

(71) Applicant: NAN YA PLASTICS CORPORATION, Taipei (TW)

(72) Inventors: Te-Chao Liao, Taipei (TW); Meng-Huai Han, Taipei (TW); Chi-Lin Chen, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 17/527,166

(22) Filed: Nov. 16, 2021

(30) Foreign Application Priority Data

Oct. 7, 2021 (TW) .................. 110137406

(51) Int. Cl.
*G01N 27/22* (2006.01)
*G01R 27/26* (2006.01)
*G16C 20/30* (2019.01)
*G16C 10/00* (2019.01)

(52) U.S. Cl.
CPC ........... *G01N 27/221* (2013.01); *G01R 27/26* (2013.01); *G01R 27/2617* (2013.01); *G16C 10/00* (2019.02); *G16C 20/30* (2019.02)

(58) Field of Classification Search
CPC .. G01N 27/221; G01R 27/26; G01R 27/2617; G16C 20/30; G16C 10/00
See application file for complete search history.

(56) References Cited

U.S. PATENT DOCUMENTS

2007/0085552 A1 4/2007 Ehata
2014/0361791 A1 * 12/2014 Park ................... G01R 27/2658
324/636

FOREIGN PATENT DOCUMENTS

| CN | 1534303 | 10/2004 |
| CN | 108595770 | 9/2018 |
| CN | 108982971 | 12/2018 |
| CN | 107368642 | 12/2019 |
| WO | WO-9706496 A1 * | 2/1997 ........... G06F 19/704 |

OTHER PUBLICATIONS

Graham Williams, "The Use of the Dipole Correlation Function in Dielectric Relaxation", Chemical Reviews, Jul. 9, 1971, pp. 55-69.
(Continued)

*Primary Examiner* — Amy He
(74) *Attorney, Agent, or Firm* — JCIPRNET

(57) ABSTRACT

A method of calculating a dielectric constant and a dielectric loss of a polymer material including the following steps is provided: providing a polymer having an optimized molecular geometry; analyzing a dipole moment autocorrelation function of the polymer having the optimized molecular geometry; fitting the dipole moment autocorrelation function of the polymer having the optimized molecular geometry via a relaxation function to obtain a corresponding fitting function; calculating a static permittivity of the polymer having the optimized molecular geometry; and obtaining a complex permittivity spectrum via the fitting function and the static permittivity, so as to calculate a corresponding dielectric constant and dielectric loss of the polymer having the optimized molecular geometry.

8 Claims, 2 Drawing Sheets

(56) References Cited

OTHER PUBLICATIONS

Grant D. Smith et al., "A molecular-dynamics simulation study of dielectric relaxation in a 1,4-polybutadiene melt", The Journal of Chemical Physics, Dec. 8, 2002, pp. 1-11.
"Office Action of Taiwan Counterpart Application", dated Jun. 20, 2022, p. 1-p. 5.

* cited by examiner

US 11,579,109 B1

METHOD OF CALCULATING DIELECTRIC CONSTANT AND DIELECTRIC LOSS OF POLYMER MATERIAL

CROSS-REFERENCE TO RELATED APPLICATION

This application claims the priority benefit of Taiwan application serial no. 110137406, filed on Oct. 7, 2021. The entirety of the above-mentioned patent application is hereby incorporated by reference herein and made a part of this specification.

BACKGROUND OF THE INVENTION

Field of the Invention

The invention relates to a calculation method of a polymer material, and particularly relates to a method of calculating the dielectric constant (Dk) and the dielectric loss (Df) of a polymer material.

Description of Related Art

With the development of wireless communication, radio frequency identification techniques at a wave band of 2 GHz or less have become saturated. Therefore, in future techniques, it may be necessary to move towards higher frequency wave bands. Generally speaking, the use of millimeter wave frequency bands (such as 30 GHz to 300 GHz) is a consensus in this field. Therefore, in wireless communication transmission, the corresponding increase in operating frequency and/or transmission speed often requires the use of materials with low dielectric constant and low dielectric loss to improve signal delay and/or reduce signal transmission loss.

Generally, to understand the physical properties of a polymer, it is often necessary to obtain the polymer first via synthesis or other suitable methods. Then, the corresponding physical quality measurement of the polymer is performed.

Current experiments usually adopt a resonant cavity to measure the dielectric constant or the dielectric loss of a material. However, in general, the wave band that is usually measured by the resonant cavity is 2 GHz, 5 GHz, or 10 GHz. Moreover, such measurement often requires the provision of corresponding polymers/polymer materials. Therefore, the application thereof takes a longer time to prepare and/or higher preparation cost.

SUMMARY OF THE DISCLOSURE

The invention provides a calculation method of a polymer material that may be used to calculate the dielectric constant and the dielectric loss of a polymer material.

A method of calculating a dielectric constant and a dielectric loss of a polymer material of the invention including the following steps is provided: providing a polymer having an optimized molecular geometry; analyzing a dipole moment autocorrelation function of the polymer having the optimized molecular geometry; fitting the dipole moment autocorrelation function of the polymer having the optimized molecular geometry via a relaxation function to obtain a corresponding fitting function; calculating a static permittivity of the polymer having the optimized molecular geometry; and obtaining a complex permittivity spectrum via the fitting function and the static permittivity, so as to calculate a corresponding dielectric constant and dielectric loss of the polymer having the optimized molecular geometry.

In an embodiment of the invention, the polymer has a halogen functional group or a cyanate ester functional group.

In an embodiment of the invention, the polymer has a molecular weight between 2500 and 3500.

In an embodiment of the invention, the polymer has a halogen functional group or a cyanate ester functional group and a molecular weight between 2500 and 3500.

In an embodiment of the invention, the relaxation function is a KWW relaxation function.

In an embodiment of the invention, the method calculates a corresponding dielectric constant and dielectric loss of a polymer material in an electromagnetic wave band from 1 GHz to 500 GHz.

In an embodiment of the invention, the method further includes the following steps: providing the polymer having an initial guess molecular geometry; and performing a geometric structure optimization via the polymer having the initial guess molecular geometry to obtain the polymer having the optimized molecular geometry.

In an embodiment of the invention, the method is at least executed by a computer. The computer includes an input unit, an output unit, and a processing unit. The input unit is adapted to input the polymer having the initial guess molecular geometry. The output unit is adapted to present a corresponding dielectric constant and dielectric loss of the polymer having the optimized molecular geometry. The processing unit is connected to the input unit and the output unit by a signal.

Based on the above, via the method of the invention, the dielectric constant and the dielectric loss of the polymer/polymer material may be calculated and/or estimated before the corresponding polymer/polymer material is synthesized.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

The terminology used in the specification is only for the object of describing specific embodiments and is not limiting. As used herein, unless the content clearly indicates otherwise, the singular forms "a", "one", and "the" are intended to include the plural form, including "at least one". "Or" means "and/or". As used in the specification, the term "and/or" includes any and all combinations of one or a plurality of the associated listed items.

Unless otherwise stated, all of the terminology used in the present specification (including technical and scientific terminology) have the same definition as those commonly understood by those skilled in the art of the invention. It should be further understood that, terminology defined in commonly-used dictionaries should be interpreted to have the same definitions in related art and in the entire specification of the invention, and are not interpreted as ideal or overly-formal definitions unless clearly stated as such in the present specification.

Figure 1:
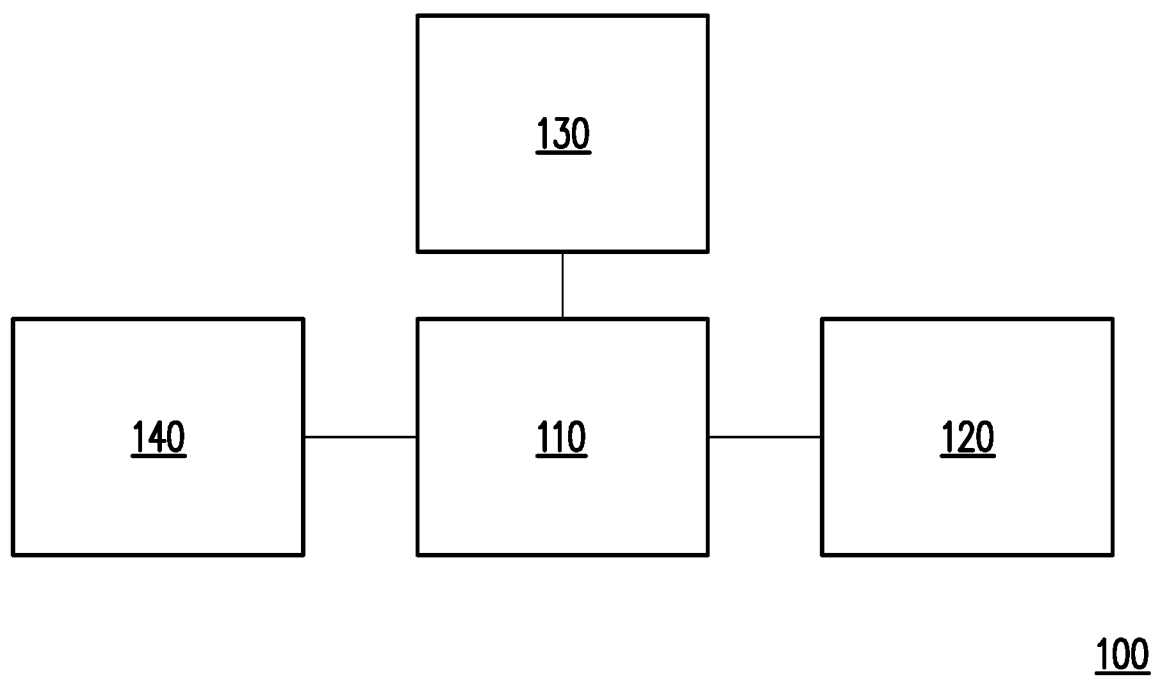
FIG. 1 is a schematic diagram of a computer suitable for calculating the dielectric constant and the dielectric loss of a polymer material according to an embodiment of the invention.

Please refer to FIG. 1. FIG. 1 is an exemplary illustration of a computer suitable for calculating the dielectric constant and the dielectric loss of a molecule/polymer/polymer material.

Please refer to FIG. 1, a computer 100 may include corresponding hardware or software. Taking hardware as an example, the computer 100 may include an input unit 120, an output unit 130, a processing unit 110, and a storage unit 140. At least two of the input unit 120, the output unit 130, the processing unit 110, and the storage unit 140 may be connected by a signal via a signal line in a wired signal transmission manner, but the invention is not limited thereto. In an embodiment, at least two of the input unit 120, the output unit 130, the processing unit 110, and the storage unit 140 may be connected by a signal in a wireless signal transmission manner. In other words, the signal connection mentioned in the invention may generally refer to the connection method of wired signal transmission or wireless signal transmission. In addition, the invention does not limit all signal connection methods to be the same or different.

In the present embodiment, the input unit 120 may include a mouse, a keyboard, a touch panel, and/or a device suitable for data/data input via a graphical user interface (GUI), but the invention is not limited thereto. In an embodiment, the input unit 120 may include a virtual-reality input unit 120. For example, the input unit 120 may include a signal receiving element (such as a communication chip, a communication antenna, and/or a communication port), and parameters or commands may be transmitted to a control unit via the input unit 120 in a remote-control method.

In the present embodiment, the output unit 130 may include a screen, a printer, and/or a device suitable for presenting a graphical user interface, but the invention is not limited thereto. In an embodiment, the output unit 130 may include a virtual-reality output unit 130. For example, the output unit 130 may include a signal transmission element (such as a communication chip, a communication antenna, and/or a communication port) to directly or indirectly transmit the corresponding parameter or data from the output unit 130 to the user or operator, so that the user or operator may learn the corresponding parameter or data.

In the present embodiment, the storage unit 140 may include a memory, a hard disk, a disk array, a cloud system that may store relevant data, and/or other electronic elements or devices that may store data temporarily or permanently, but the invention is not limited thereto. In an embodiment, the data may be directly or indirectly processed by the processing unit 110 for data processing and/or data calculation.

In the present embodiment, the processing unit 110 may include a central processing unit (CPU), a graphics processing unit (GPU), a tensor processing unit (TPU), and/or a neural-network processing unit (NPU), but the invention is not limited thereto. The processing unit 110 may perform a corresponding operation according to an instruction input via the output unit 130, and store the results in the operations in the storage unit 140 and/or present the results to the user or the operator via the output unit 130.

In the present embodiment, the software may include corresponding commercial software and/or software compiled/coded by users/operators according to their needs, but the invention is not limited thereto. Commercial software includes, for example, a corresponding operating system and/or computational chemistry software suitable for molecular calculation, but the invention is not limited thereto. The computational chemistry software may include a general atomic and molecular electronic structure system (GAMESS), Chemistry at HARvard Macromolecular Mechanics (CHARMm), Materials Studio, or other suitable software, but the invention is not limited thereto.

Figure 2:
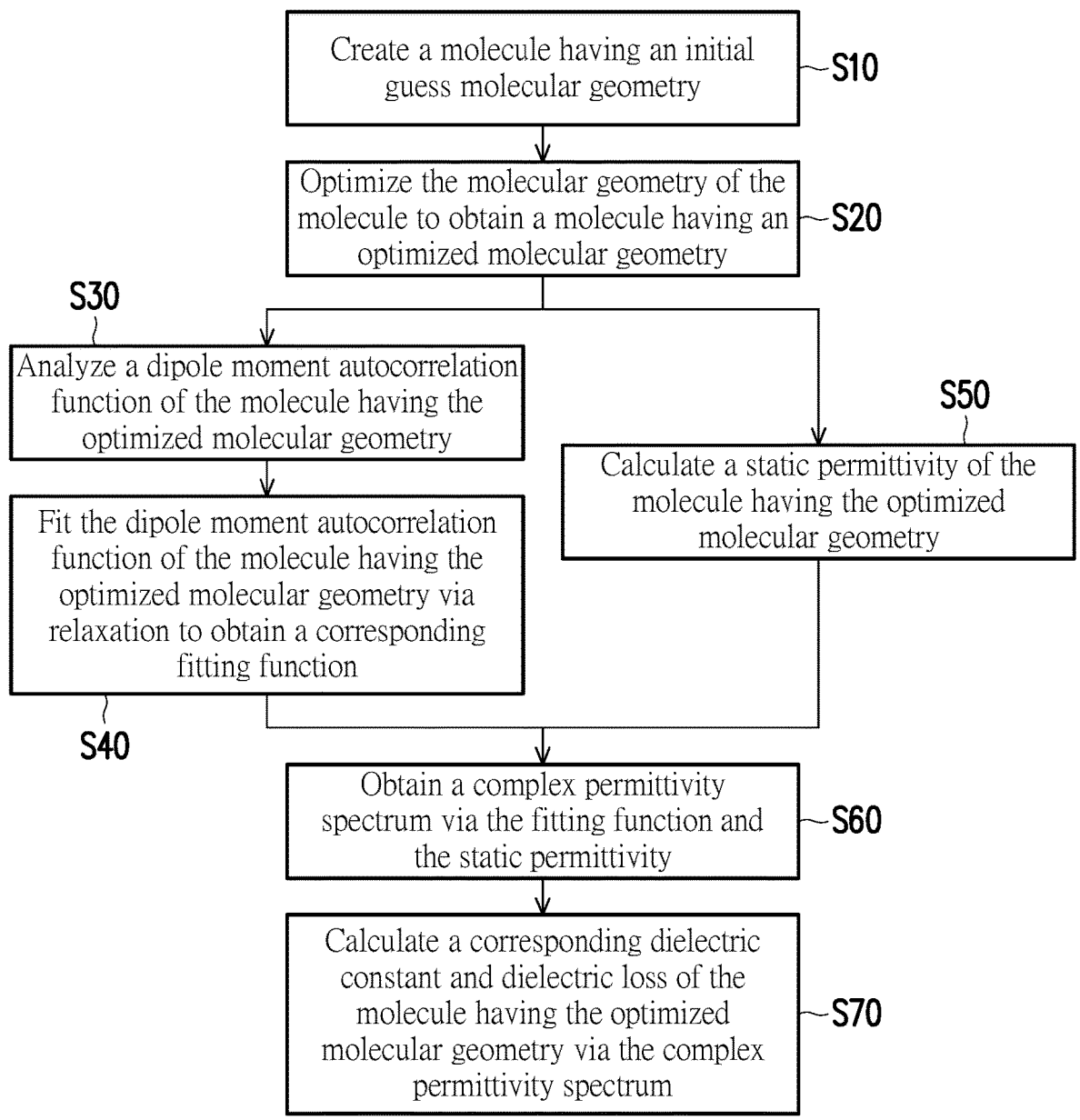
FIG. 2 is a schematic partial flowchart of a method of calculating the dielectric constant and the dielectric loss of a polymer material according to an embodiment of the invention.

Referring to FIG. 2, a method of calculating the dielectric constant and the dielectric loss of a molecule/polymer/polymer material of an embodiment of the invention may be illustrated as follows.

Step S10: a molecule/polymer having a corresponding initial guess molecular geometry is created. The initial guess molecular geometry may be presented in the form of a Cartesian coordinate system or a Z-matrix, but the invention is not limited thereto. After the initial guess molecular structure is input to a computer (such as the computer 100) via an output unit (such as the output unit 130), adaptive calculations may be performed via a processing unit (such as the processing unit 110). The method of creating the initial guess molecular geometry should be prior art in the field of computational chemistry, and is therefore not repeated herein. For example, the corresponding initial guess molecular geometry of a molecule/polymer may be created by the Visualizer module in the Materials Studio software.

Step S20: a molecule/polymer having an optimized molecular geometry is provided. The corresponding potential energy of a molecule/polymer having the optimized molecular geometry may be located at a local minimum on the potential energy surface. The geometry optimization calculation of the molecule/polymer may be adjusted according to the properties of the molecule/polymer calculation performed subsequently, and is not limited in the invention. Taking the electrical properties of the molecule/polymer as an example, a corresponding unit cell model may be created using the Amorphous Cell module in the Materials Studio software via the initial guess molecular geometry created above. Then, energy optimization, high-temperature annealing, and/or dynamic equilibrium are/is performed on the model using the Forcite module in the Materials Studio software to obtain the optimized molecular geometry of the molecule/polymer.

Step S30: the dipole moment autocorrelation function (DACF) of the molecule/polymer having the optimized molecular geometry is analyzed. The analysis method may be adjusted according to the calculation performance of the computer and/or the corresponding software, and is not limited in the invention. For example, the dipole moment autocorrelation function of the molecule/polymer having the optimized molecular geometry may be analyzed using the Forcite module in the Materials Studio software.

Step S40: the dipole moment autocorrelation function of the molecule/polymer having the optimized molecular geometry is fitted via a relaxation function to obtain a corresponding fitting function. In an embodiment, the relaxation function used may include a Kohlrausch-Williams-Watts relaxation function (KWW relaxation function), but the invention is not limited thereto.

In an embodiment, a form of the relaxation function may be represented by the following [Equation 1].

$$\Phi = A\exp\left(-\left(\frac{t}{\tau_{KWW}}\right)^B\right) \quad \text{[Equation 1]}$$

In particular, in [Equation 1], A and B are the corresponding fitting parameters, t is the time, and $\tau_{KWW}$ is the corresponding relaxation time.

Step S50: the static permittivity of the molecule/polymer having the optimized molecular geometry is calculated. Generally speaking, the relationship between the total dipole moment of the molecule/polymer and the corresponding static permittivity may be represented by the following [Equation 2].

$$\epsilon_0 = \epsilon_\infty + \frac{4\pi}{3}\frac{\langle M^2 \rangle - \langle M \rangle^2}{Vk_BT} \quad \text{[Equation 2]}$$

In particular, in [Equation 2], $\varepsilon_0$ is the corresponding static permittivity, $\varepsilon_\infty$ is the corresponding optical permittivity, M is the total dipole moment of the molecule/polymer, V is the corresponding volume of the molecule/polymer (usually: Van der Waals volume), $k_B$ is the Boltzmann constant, and T is the corresponding temperature. For commonly used dielectric materials, the optical dielectric constant of the corresponding molecule/polymer may usually be close to 1 or directly regarded as 1.

Also, the dipole moment autocorrelation function may be a polarization decay function, and may be represented by the following [Equation 3].

$$\Phi(t) = \frac{\langle M(0) \cdot M(t) \rangle}{\langle M(0) \cdot M(0) \rangle} \quad \text{[Equation 3]}$$

In particular, in [Equation 3], $\Phi(t)$ is the dipole moment autocorrelation function, and M(t) is the corresponding dipole moment at time t.

In an embodiment, the corresponding static permittivity and/or dipole moment autocorrelation function of the molecule/polymer having the optimized molecular geometry may be obtained by a general molecular dynamics simulation software. For example, the corresponding dipole moment autocorrelation function of a molecule/polymer having a geometry may be obtained using the Forcite module in the Materials Studio software.

Step S60: a complex permittivity spectrum is obtained via the fitting function and the static permittivity. Generally speaking, according to the dielectric relaxation theory, the superposition relationship of the complex permittivity of a dielectric substance may be represented by the following [Equation 4].

$$\frac{\epsilon^*(i\omega) - \epsilon_\infty}{\epsilon_0 - \epsilon_\infty} = \int_0^\infty dt[e^{-i\omega t}]\left[-\frac{d\Phi(t)}{dt}\right] = 1 - i\omega\int_0^\infty dt[e^{-i\omega t}]\Phi(t) \quad \text{[Equation 4]}$$

In particular, in [Equation 4], $\varepsilon_0$ is the corresponding static permittivity, and $\varepsilon_\infty$ is the corresponding optical permittivity. In the corresponding physical meaning, the static permittivity may correspond to the permittivity of the dielectric substance in an electric field of extremely low frequency (such as: the frequency is 0 or close to 0), and the optical permittivity may correspond to the permittivity of the dielectric substance in an electric field of extremely high frequency (for example, the frequency is infinite).

Step S70: a corresponding dielectric constant and dielectric loss of the molecule/polymer having the optimized molecular geometry is calculated via the complex permittivity spectrum. Specifically, the corresponding static permittivity of the molecule/polymer having the optimized molecular geometry (for example: corresponding to the result of [Equation 2]) and/or dipole moment autocorrelation function (for example: corresponding to the result of [Equation 3]) may be entered into the complex permittivity spectrum relational equation obtained by the fitting function and the static permittivity (for example: corresponding to [Equation 4]). In this way, the corresponding dielectric constant value and the corresponding dielectric loss value of the molecule/polymer having the optimized molecular geometry in the corresponding frequency range may be deduced. Specifically, in the complex function (i.e., exp(-iωt)) in [Equation 4], the real part value may correspond to the dielectric constant (Dk), and the imaginary part value divided by the real part value (i.e., imaginary part value/real part value) may correspond to the dielectric loss value (Df).

The above theoretical part is as provided in the following literature: Chemical Reviews, 1972, Vol. 472, No. 1 p55-69 and/or J. Chem. Phys., 117, 10350 (2002).

In an embodiment, via the above method and calculating via the KWW relaxation function, after the molecule/polymer having a halogen functional group or a cyanate ester functional group in the electromagnetic wave band range from 1 GHz to 500 GHz is calculated, better (such as closer to experimental values) dielectric constant and dielectric loss may be obtained.

In an embodiment, via the above method and calculating via the KWW relaxation function, after the polymer molecule/polymer having a molecular weight between 2500 and 3500 in the electromagnetic wave band range of 1 GHz to 500 GHz is calculated, better (such as closer to experimental values) dielectric constant and dielectric loss may be obtained.

In an embodiment, the result (such as the corresponding dielectric constant and/or dielectric loss) obtained via the above method may be presented by an output unit (such as the output unit 130).

Based on the above, via the method of the invention, the dielectric constant and the dielectric loss of a molecule/polymer may be calculated and/or estimated. In this way, before the corresponding molecule/polymer is synthesized, the dielectric constant and the dielectric loss of the molecule/polymer/polymer material may be estimated in advance via the method of the invention. Therefore, the efficiency of production or synthesis may be improved.

EMBODIMENTS

The embodiments shown below are used to specifically explain the invention, but the invention is not limited by the following embodiments at all.

In the following embodiments, polymer A is a fluoropolymer (such as Teflon) having a molecular weight of about 2500 to 3500. The chemical formula of polymer A may be as shown in the following [Chemical formula 1].

[Chemical formula 1]

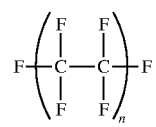

In [Chemical formula 1], n may be an integer greater than or equal to 25 and less than or equal to 34. In actual application, due to the manufacturing process (such as: the purity of the reactants, the purity of the reaction environment, or other factors that may affect the purity of the product, but not limited thereto), and/or due to the use process (such as: contact with other substances, scraping, grinding, cutting, or other applicable use methods, but not limited thereto), a small portion of the fluorine atoms in the Teflon polymer may be replaced by hydrogen atoms, deuterium atoms, or other possible atoms (such as chlorine atoms, but not limited thereto). However, the small amount of substitution may still be reasonably and/or equally regarded as a Teflon polymer without affecting or very slightly affecting the use, physical properties, and/or chemical properties of the Teflon polymer.

In the following embodiments, polymer B is a cyanate ester-containing polymer having a molecular weight of about 2500 to 3500. The chemical formula of polymer B may be as shown in the following [Chemical formula 2].

[Chemical formula 2]

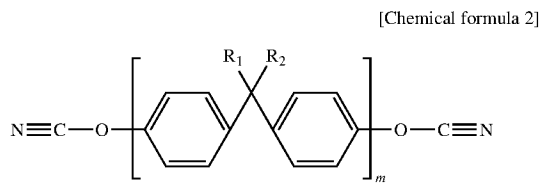

In [Chemical formula 2], m may be an integer greater than or equal to 11 and less than or equal to 22. In [Chemical formula 2], $R_1$ and $R_2$ may be hydrogen, deuterium, methyl, or ethyl, respectively.

Embodiment 1

In [Embodiment 1], in order to calculate the dielectric constant and the dielectric loss of the molecule/polymer via the above method, the difference is that a relaxation function D and a relaxation function E, which are different from the KWW relaxation function, are used. The relaxation function D may be represented by the following [Equation 5], which may be a simple exponential decay function. The relaxation function E may be represented by the following [Equation 6], which may be a double exponential decay function.

$$A_1 \exp\left(\frac{-t}{\tau_1}\right) \quad \text{[Equation 5]}$$

In particular, in [Equation 5], $A_1$ is the corresponding fitting parameter, t is the time, and $\tau_1$ is the corresponding relaxation time.

$$A_2 \exp\left(\frac{-t}{\tau_2}\right) + A_3 \exp\left(\frac{-t}{\tau_3}\right) \quad \text{[Equation 6]}$$

In particular, in [Equation 6], $A_2$ and $A_3$ are respectively the corresponding fitting parameters, t is the time, and $\tau_1$ and $\tau_2$ are the corresponding relaxation times.

In addition, the comparison between the calculation results of [Embodiment 1] and the experimental values is listed in the following [Table 1]. In particular, in the results listed in [Table 1], the corresponding parameter/relaxation time of each relaxation function are already optimized to be closest to the corresponding experimental values.

TABLE 1

| Dk/Df | Experimental value | KWW relaxation function | Relaxation function D | Relaxation function E |
|---|---|---|---|---|
| Polymer A | 2.03/0.0003 | 2.01/0.0005 | 2.01/0.00001 | 2.01/0.0004 |
| Polymer B | 2.64/0.0027 | 2.27/0.0076 | 2.27/0.1581 | 2.27/0.0147 |

As shown in [Table 1], for polymers with a molecular weight between 2500 and 3500 and having a halogen functional group (such as polymer A) or polymers having a cyanate ester functional group (such as polymer B), the use of KWW relaxation function for fitting may produce better calculation results.

Embodiment 2

In [Embodiment 2], to calculate the dielectric constant and the dielectric loss of the molecule/polymer via the above method, and to use the KWW relaxation function for fitting, the difference is: the parameters (such as parameter A and parameter B in [Equation 1]) and the relaxation time (such as: $\tau_{KWW}$ in [Equation 1]) in the KWW relaxation function (such as [Equation 1]) are respectively adjusted. In addition, the comparison between the calculation results of [Embodiment 2] and the experimental values is listed in the following [Table 2] and [Table 3].

TABLE 2

| Dk/Df | Experimental value | Value of parameter A/0.5 to 1.0 | Value of parameter B/0.0 to 1.0 | Value of $\tau_{KWW}$/ 0.0 to 0.5 |
|---|---|---|---|---|
| Polymer A | 2.03/0.0003 | | 2.01/0.0005 | |
| Polymer B | 2.64/0.0027 | | 2.27/0.0076 | |

TABLE 3

| Dk/Df | Experimental value | Value of parameter A/0.0 to 0.5 | Value of parameter B/1.0 to 2.0 | Value of $\tau_{KWW}$/ 0.5 to 1.0 |
|---|---|---|---|---|
| Polymer A | 2.03/0.0003 | | 2.01/0.0008 | |
| Polymer B | 2.64/0.0027 | | 2.27/0.0094 | |

As shown in [Table 2] and [Table 3], for polymers with a molecular weight between 2500 and 3500 and having a halogen functional group (such as polymer A) or polymers having a cyanate ester functional group (such as polymer B), when the KWW relaxation function is used for fitting, the preferred parameter range/relaxation time is A: 0.5 to 1.0, B: 0.0 to 1.0, and $\tau_{KWW}$: 0.0 to 0.5.

As shown in the above [Embodiments], via the method of the invention, in the method of calculating the dielectric constant and the dielectric loss of a molecule/polymer/polymer material of the invention, the calculated and/or estimated dielectric constant and dielectric loss of the molecule/polymer may be close to the corresponding experimental values. Preferably, the method of the invention may be applied to a molecule/polymer having a halogen functional group or a cyanate ester functional group, and polymer molecule with a molecular weight between 2500 and 3500, and/or corresponding to the dielectric constant and the dielectric loss of the molecule in the electromagnetic wave band from 1 GHz to 500 GHz.

INDUSTRIAL APPLICABILITY

In the method of the invention, the dielectric constant and the dielectric loss of the molecule/polymer/polymer material may be calculated and/or estimated before the corresponding molecule/polymer is synthesized. Therefore, the efficiency of production or synthesis may be improved. Moreover, via the method of the invention, whether a material or a molecule/polymer/polymer material is suitable for high-frequency (such as: 1 GHz to 500 GHz electromagnetic wave band) wireless communication transmission may be evaluated in advance.

What is claimed is:

1. A method of calculating a dielectric constant and a dielectric loss of a polymer material, comprising:
   providing a polymer having an optimized molecular geometry;
   analyzing a dipole moment autocorrelation function of the polymer having the optimized molecular geometry;
   fitting the dipole moment autocorrelation function of the polymer having the optimized molecular geometry via a relaxation function to obtain a corresponding fitting function;
   calculating a static permittivity of the polymer having the optimized molecular geometry; and
   obtaining a complex permittivity spectrum via the fitting function and the static permittivity to calculate a corresponding dielectric constant and dielectric loss of the polymer having the optimized molecular geometry.

2. The method of calculating the dielectric constant and the dielectric loss of the polymer material of claim 1, wherein the polymer has a halogen functional group or a cyanate ester functional group.

3. The method of calculating the dielectric constant and the dielectric loss of the polymer material of claim 1, wherein the polymer has a molecular weight between 2500 and 3500.

4. The method of calculating the dielectric constant and the dielectric loss of the polymer material of claim 1, wherein the polymer has a halogen functional group or a cyanate ester functional group and a molecular weight between 2500 and 3500.

5. The method of calculating the dielectric constant and the dielectric loss of the polymer material of claim 1, wherein the relaxation function is a KWW relaxation function.

6. The method of calculating the dielectric constant and the dielectric loss of the polymer material of claim 1, wherein the method calculates a corresponding dielectric constant and dielectric loss of a polymer material in an electromagnetic wave band from 1 GHz to 500 GHz.

7. The method of calculating the dielectric constant and the dielectric loss of the polymer material of claim 1, further comprising:
   providing the polymer having an initial guess molecular geometry; and
   performing a geometric structure optimization via the polymer having the initial guess molecular geometry to obtain the polymer having the optimized molecular geometry.

8. The method of calculating the dielectric constant and the dielectric loss of the polymer of claim 7, wherein the method is at least executed by a computer, and the computer comprises:
   an input unit adapted to input the polymer having the initial guess molecular geometry;
   an output unit adapted to present a corresponding dielectric constant and dielectric loss of the polymer having the optimized molecular geometry; and
   a processing unit connected to the input unit and the output unit by a signal.

* * * * *